United States Patent
Drozdzal et al.

(10) Patent No.: US 9,514,556 B2
(45) Date of Patent: Dec. 6, 2016

(54) SYSTEM AND METHOD FOR DISPLAYING MOTILITY EVENTS IN AN IN VIVO IMAGE STREAM

(71) Applicant: GIVEN IMAGING LTD., Yoqneam (IL)

(72) Inventors: Michal Drozdzal, Wroclaw (PL); Santiago Segui Mesquida, Barcelona (ES); Petia Radeva, Barcelona (ES); Jordi Vitria, Barcelona (ES); Laura Igual-Munoz, Barcelona (ES); Carolina Malagelada, Barcelona (ES); Fernando Azpiroz, Barcelona (ES)

(73) Assignee: GIVEN IMAGING LTD., Yoqneam (IL)

( * ) Notice: Subject to any disclaimer, the term of this patent is extended or adjusted under 35 U.S.C. 154(b) by 261 days.

(21) Appl. No.: 14/375,318

(22) PCT Filed: Jan. 30, 2013

(86) PCT No.: PCT/IL2013/050081
§ 371 (c)(1),
(2) Date: Jul. 29, 2014

(87) PCT Pub. No.: WO2013/114361
PCT Pub. Date: Aug. 8, 2013

(65) Prior Publication Data
US 2015/0016700 A1    Jan. 15, 2015

Related U.S. Application Data

(60) Provisional application No. 61/592,786, filed on Jan. 31, 2012.

(51) Int. Cl.
*G06K 9/00* (2006.01)
*G06T 11/60* (2006.01)
(Continued)

(52) U.S. Cl.
CPC .......... *G06T 11/60* (2013.01); *A61B 1/00009* (2013.01); *A61B 1/00045* (2013.01); *A61B 1/041* (2013.01);
(Continued)

(58) Field of Classification Search
None
See application file for complete search history.

(56) References Cited

U.S. PATENT DOCUMENTS

| 5,519,828 A | 5/1996 | Rayner |
| 6,944,316 B2 | 9/2005 | Glukhovsky et al. |

(Continued)

FOREIGN PATENT DOCUMENTS

WO    WO/2007/105213    9/2007

OTHER PUBLICATIONS

Bejakovic et al. "Analysis of Crohn's Disease Lesions in Capsule Endoscopy Images" 2009 IEEE International Conference on Robotics and Automation Kobe International Conference Center pp. 2793-2798 May 12-17, 2009.

(Continued)

*Primary Examiner* — Weiwen Yang
(74) *Attorney, Agent, or Firm* — Pearl Cohen Zedek Latzer Baratz LLP

(57) ABSTRACT

A system and method may analyse and display intestinal motility events, based on an image stream captured by an in vivo imaging device. According to some embodiments, the system includes a storage unit to store image frames from the image stream, a processor to select a strip of pixels from a plurality of image frames of the image stream and to align the selected strips adjacently to form a motility events bar, and a visual display unit for displaying the motility events bar to a user.

20 Claims, 8 Drawing Sheets

(51) Int. Cl.
*A61B 1/00* (2006.01)
*A61B 1/04* (2006.01)
*G06F 19/00* (2011.01)
*G06T 7/00* (2006.01)

(52) U.S. Cl.
CPC ......... *G06F 19/321* (2013.01); *G06F 19/3406* (2013.01); *G06K 9/00523* (2013.01); *G06T 7/0016* (2013.01); *G06T 2207/30028* (2013.01); *G06T 2207/30092* (2013.01)

(56) References Cited

U.S. PATENT DOCUMENTS

| | | | |
|---|---|---|---|
| 7,009,634 | B2 | 3/2006 | Iddan et al. |
| 7,215,338 | B2 | 5/2007 | Horn et al. |
| 7,474,327 | B2 | 1/2009 | Davidson et al. |
| 7,813,538 | B2 * | 10/2010 | Carroll ............... A61B 1/00009 382/128 |
| 7,986,337 | B2 | 7/2011 | Davidson et al. |
| 8,068,897 | B1 | 11/2011 | Gazdzinski |
| 8,144,152 | B2 | 3/2012 | Horn et al. |
| 8,335,362 | B2 | 12/2012 | Vilarino et al. |
| 8,340,745 | B2 * | 12/2012 | Balas ................... A61B 5/0059 600/476 |
| 2005/0094017 | A1 | 5/2005 | Hirakawa |
| 2006/0074275 | A1 | 4/2006 | Davidson et al. |
| 2007/0060798 | A1 | 3/2007 | Krupnik et al. |
| 2007/0118012 | A1 | 5/2007 | Gilad |
| 2010/0053313 | A1 | 3/2010 | Horn et al. |
| 2011/0305377 | A1 | 12/2011 | Drozdzal et al. |
| 2012/0013773 | A1 * | 1/2012 | Yoshino ............... A61B 1/0638 348/241 |

OTHER PUBLICATIONS

Ciaccio et al. "Distinguishing Patients With Celiac Disease by Quantitative Analysis of Video Capsule Endoscopy Images" Computer Methods and Programs in Biomedicine vol. 100, Issue 1, Oct. 2010, pp. 39-48.
Coimbra, Miguel Tavares "MPEG-7 Visual Descriptors—Contributions for Automated Feature Extraction in Capsule Endoscopy" IEEE Transactions on Circuits and Systems for Video Technology, Vol. 16, No. 5, May 2006.
Felzenszwalb et al. "Dynamic Programming and Graph Algorithms in Computer Vision" IEEE Transactions on Pattern Analysis and Machine Intelligence, Vol. 33, No. 4, Apr. 2011.
Freire, Fernando Luis Vilariño "A Machine Learning Approach for Intestinal Motility Assessment with Capsule Endoscopy" Doctoral Dissertation, Jun. 12, 2006, Universitat Autònoma de Barcelona, Printed by Ediciones Gráficas Rey, S.L.
Hai et al. "Adaptive Control of Video Display for Diagnostic Assistance by Analysis of Capsule Endoscopic Images" ICPR 2006 Proceedings of the 18th International Conference on Pattern Recognition—vol. 03 pp. 980-983.
Iddan et al. "Wireless Capsule Endoscopy" Nature vol. 405 pp. 417-418 May 25, 2000.
Jung et al. "Active Blood Detection in a High Resolution Capsule Endoscopy using Color Spectrum Transformation" International Conference on BioMedical Engineering and Informatics vol. 1 pp. 859-862, 2008.
Kang et al. "Real-Time Image Processing System for Endoscopic Applications" Electrical and Computer Engineering, 2003. IEEE CCECE 2003. Canadian Conference on vol. 3 pp. 1469-1472.
Karkanis et al. "Computer-Aided Tumor Detection in Endoscopic Video Using Color Wavelet Features" IEEE Transactions on Information Technology in Biomedicine, Vol. 7, No. 3, Sep. 2003, pp. 141-152.
Li et al. "Computer-Based Detection of Bleeding and Ulcer in Wireless Capsule Endoscopy Images by Chromaticity Moments" Computers in Biology and Medicine vol. 39, Issue 2, Feb. 2009, pp. 141-147.
Mackiewicz et al. "Colour and Texture Based Gastrointestinal Tissue Discrimination" Acoustics, Speech and Signal Processing, 2006. ICASSP 2006 Proceedings. 2006 IEEE International Conference on vol. 2 Issue. II pp. 597-600.
Mackiewicz, Michal "Computer-assisted Wireless Capsule Endoscopy video analysis" Doctoral Thesis, Dec. 3, 2007, University of East Anglia.
Malagelada et al. "Functional Gut Disorders or Disordered Gut Function? Small Bowel Dysmotility Evidenced by an Original Technique" Neurogastroenterology & Motility vol. 24, Issue 3, pp. 223-e105, Mar. 2012.
Malagelada et al. "New Insight Into Intestinal Motor Function via Noninvasive Endoluminal Image Analysis " Gastroenterology, vol. 135, Issue 4 , pp. 1155-1162, Oct. 2008.
Shahn et al. "Classification of Bleeding Images in Wireless Capsule Endoscopy using HSI Color Domain and Region Segmentation" Proceeding of 2007 New England American Society for Engineering Education Conference, Kingston, RI, pp. 1-7, Apr. 2007.
Szczypiński et al. "A Model of Deformable Rings for Interpretation of Wireless Capsule Endoscopic Videos" Medical Image Analysis vol. 13, Issue 2, pp. 312-324, Apr. 2009.
Vilariño et al. "Intestinal Motility Assessment With Video Capsule Endoscopy: Automatic Annotation of Phasic Intestinal Contractions" IEEE Transactions on Medical Imaging, vol. 29, No. 2, pp. 246-259 Feb. 2010.
Vu et al. "Contraction Detection in Small Bowel from an Image Sequence of Wireless Capsule Endoscopy" MICCAI 2007, Part I, LNCS 4791, pp. 775-783, 2007.
Vu et al. "Detection of contractions in adaptive transit time of the small bowel from wireless capsule endoscopy videos" Comput Biol Med. Jan. 2009;39(1):16-26. Epub Dec. 4, 2008.
Vu et al. "Evaluating the Control of the Adaptive Display Rate for Video Capsule Endoscopy Diagnosis" Proceedings of the 2008 IEEE International Conference on Robotics and Biomimetics Bangkok, Thailand, Feb. 21-26, pp. 74-79, 2009.
Whitehead, William E. "Gastrointestinal Motility Disorders of the Small Intestine, Large Intestine, Rectum, and Pelvic Floor" Publisher: IFFGD, 2001.
Yagi et al. "A Diagnosis Support System for Capsule Endscopy" Inflammopharmacology 15(2):78-83, Apr. 2007.
Hwang et al., "Blood Detection in Wireless Capsule Endoscopy using Expectation Maximization Clustering", Medical Imaging 2006: Image Processing, Proceedings of SPIE, vol. 6144, pp. 61441P-1-11 (2006).
Quigley, "Gastric and Small Intestinal Motility in Health and Disease", Gastrointestinal Motility in Clinical Practice, vol. 25, No. 1, Mar. 1996, pp. 113-145.

* cited by examiner

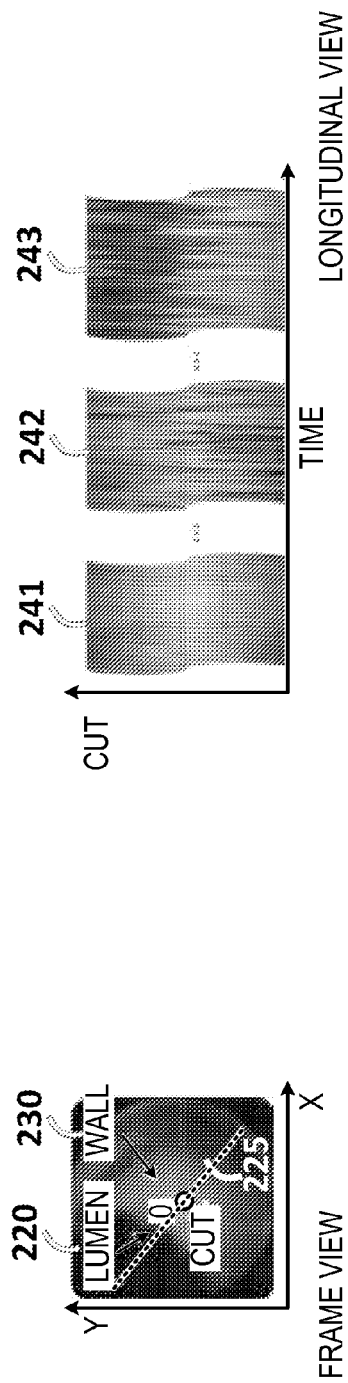
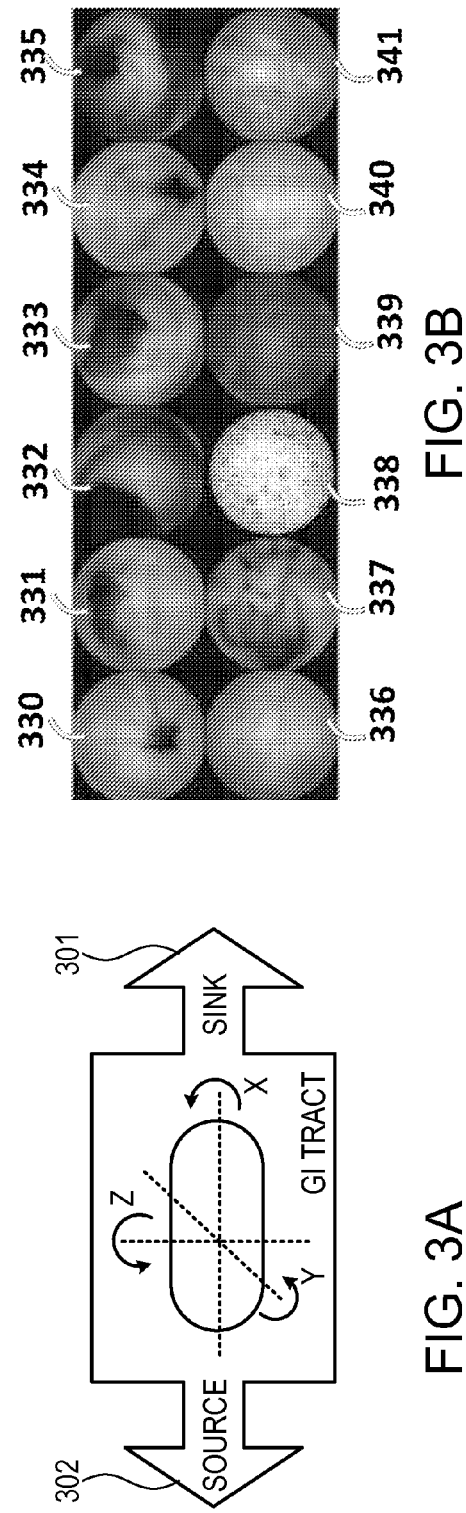

SYSTEM AND METHOD FOR DISPLAYING MOTILITY EVENTS IN AN IN VIVO IMAGE STREAM

CROSS-REFERENCE TO RELATED APPLICATIONS

This application is a National Phase Application of PCT International Application No. PCT/IL2013/050081, entitled "SYSTEM AND METHOD FOR DISPLAYING MOTILITY EVENTS IN AN IN VIVO IMAGE STREAM", International Filing Date Jan. 30, 2013, published on Aug. 8, 2013 as International Publication No. WO 2013/114361, which in turn claims priority from U.S. Provisional Patent Application No. 61/592,786, filed Jan. 31, 2012, all of which are incorporated herein by reference in their entirety.

FIELD OF THE INVENTION

The present invention relates to a method and system for image processing of an image stream captured in-vivo. More specifically, the present invention relates to systems and methods for analysis and display of motility events in an image stream of a gastrointestinal tract.

BACKGROUND OF THE INVENTION

The small bowel (also called small intestine) is a part of the gastrointestinal (GI) tract, connecting the stomach with the large intestine. The length of the small intestine in an adult is variable, and depending on the conditions can measure from 3 to 8 meters. The main function of the small bowel is the digestion and absorption of nutrients and minerals found in the food. In order to do so, the small intestine pushes the food through by the means of a physiological mechanism called motility.

Intestinal motility can be divided into two categories: peristalsis, e.g. synchronized movement of the intestinal wall responsible for moving the food in one direction; and independent contractions, e.g. unsynchronized movement of the intestinal wall where the muscles squeeze substantially independently of each other, which may have the effect of mixing the contents but not moving them up or down.

Intestinal motility dysfunction appears when the organ loses its ability to coordinate muscular activity, manifesting the abnormal contractile activity (e.g. spasms or intestinal paralysis). In a broad sense, any alteration in the transit of foods and secretions into the small intestine tube may be considered a motility disorder.

Manometry is currently used for gathering information for diagnosis of small intestine motility disorders. The manometry diagnosis is based on changes of intestinal wall pressure in a fixed part of the small intestine. However, this technique may have several drawbacks, for example: it is invasive, and may cause discomfort to the patient; it does not include visualization of the small intestine; only a portion of the small bowel can be evaluated; performing the manometry test may be a relatively complex procedure, and interpretation of the results may be difficult.

In-vivo imaging methods, such as performed by an in-vivo imaging system including a swallowable capsule, may be used to image body lumens within a patient. The imaging system may capture and transmit, for example, images of the gastrointestinal (GI) tract to an external recording device, while the capsule passes through the GI lumen. The capsule may capture images in variable frame rates of, for example, 1-40 frames per second. Large numbers of images, for example 100,000 to 300,000 images, may be collected for viewing during the imaging procedure, which may be performed in a duration of one to eight hours, and may be viewed and/or processed in real time. The images may be combined in sequence, and an image stream or movie of, for example, 30-120 minutes in length, may be presented to a user.

SUMMARY OF THE INVENTION

A system and method for displaying motility events or motility properties of a patient's GI tract may be useful in improving intestinal motility analysis and in diagnosing intestinal motility disorders.

A computer-implemented method is provided, according to embodiments of the present invention, for display of intestinal motility events in an image stream captured by an in vivo imaging device. The method may include receiving an image stream captured by an in vivo device. The image stream may include image frames, each frame containing a plurality of image pixels arranged in an array. A strip of pixels may be selected from each image, for example of at least a subset of images of the image stream. The selected strips may be aligned or arranged in a spatial arrangement, e.g. adjacently, to form a motility events bar. In some embodiments, the subset of images may include one or more sequences of consecutive image frames from the image stream.

The motility events bar may be displayed, on a computer monitor or display or another visual display unit. In some embodiments, the strip of pixels may include one or more lines (e.g., straight lines) of pixels selected from an image frame. A video display of the image stream may be displayed, for example alongside the motility events bar.

Different methods may be implemented for selecting strips of pixels from images to form a motility bar. In one embodiment, a fixed point in each image frame may be determined, and the selected strip of pixels may be selected to pass through the fixed point. The fixed point may be, for example, the center of the image frame. In some embodiments, the selection of pixel strips may be adaptive, and may depend on certain criteria for selection. The criteria may include, for example, detected areas or features in each image, or may include certain conditions based on image properties or pixel properties in images.

In one example, a lumen hole may be detected in each image frame (or a subset of images from the image stream), and a strip of pixels which passes through the detected lumen hole in each image frame may be selected. The selected strip may be chosen, for example, to maximize the visibility of the lumen hole in the generated motility events bar.

In another example, a red (bleeding) region of the image frame may be detected, and the strip may be selected to pass through, for example, the center of the detected region, or such that the amount of pixels passing through the detected region will be maximized in the selected strip of pixels. Other criteria for selection of pixel strips from images may include, for example, detection of regions in the image which depict turbid content, pathologies, etc. More than one criterion may be used to determine the selection of pixel strips for generation of the motility events bar.

According to some embodiments, intestinal events may be determined based on the motility events bar. The events may be determined automatically, e.g. by a processor or an intestinal events detector which may be included in or operationally connected to a processor. The detected intestinal events may include image sequences depicting a certain state of the GI lumen, for example, contractions, static closed lumen sequences, tunnel sequences and turbid lumen sequences.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein:

FIGS. 2A-2B show different types of views that may be obtained from the image stream according to an embodiment of the present invention;

FIG. 3A illustrates possible camera movements inside a body lumen according to an embodiment of the present invention;

FIG. 3B shows different in vivo images which may be captured by an imaging capsule according to an embodiment of the present invention;

Figure 1A:
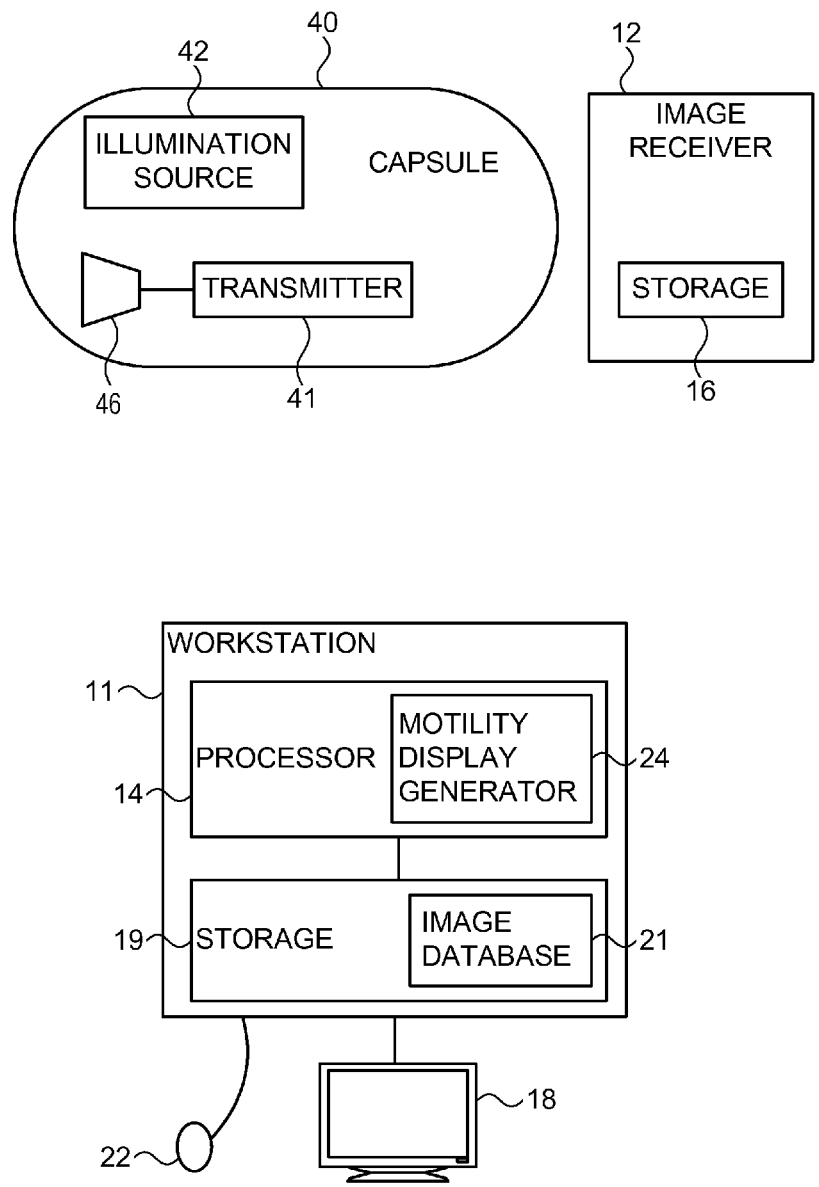
FIG. 1A shows a schematic diagram of an in-vivo imaging system according to an embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Devices according to embodiments of the present invention, including imaging, receiving, processing, storage and/or display units suitable for use with embodiments of the present invention, may be similar to embodiments described in US Patent Application Publication Number 2006/0074275, entitled "System and Method for Editing an Image Stream Captured In-Vivo", U.S. Pat. No. 7,009,634 to Iddan et al., entitled "Device for In-Vivo Imaging", and/or US Patent Application Publication Number 2007/0118012, entitled "Method of Assembling an In-Vivo Imaging Device", each assigned to the common assignee of the present application. Methods for analyzing motility within a GI tract based on comparison the images capture by an in vivo imaging capsule are disclosed, for example, in U.S. Pat. No. 6,944,316 to Glukhovsky et al. U.S. Pat. No. 7,215,338 to Horn et al. discloses a system and a method for creating a summarized graphical presentation of a data stream captured in-vivo. The graphical presentation may be in the form of a color bar. Of course, devices and systems as described herein may have other configurations and other sets of components. Devices, systems and methods according to some embodiments of the present invention may be similar to the commercial PillCam® SB2 or PillCam® Colon capsules and the associated data recorders and RAPID® workstation provided by Given Imaging, Ltd.

An in vivo imaging capsule which may be swallowed by a patient, may progress passively along the GI tract, due to peristaltic contractions which move the intestinal tissue walls. During its journey, the capsule passes through different GI organs, such as the esophagus, the stomach, the small bowel and the colon. Due to the relatively narrow tunnel structure of the small bowel tissue walls, while the capsule is traveling in the small bowel, it may maintain a position which is parallel to the direction of the tunnel. The longitudinal axis of the imaging capsule (e.g., an axis passing through the long dimension of the capsule, such as axis X in FIG. 3A) may generally remain parallel to the direction that the capsule advances in the small bowel. The imaging system of the capsule may be positioned in at least one of the longitudinal ends of the capsule, such that the imaging is performed generally in a forward and/or backward looking position, such that images of the opening and closing of the lumen are captured quite regularly. Image data capturing the opening and closing of the lumen hole, in combination with the recordation of the time of capturing each image, may permit analysis, display and/or calculation of the small bowel's motility events, or type and frequency of peristaltic activity. Embodiments of the invention may enable display of motility-related information to a medical professional in an efficient and easy to analyze way.

Reference is now made to FIG. 3A, which illustrates possible camera movements inside a body lumen. In order to analyze intestinal motility using an in vivo image stream, different characteristics may be considered, such as complex appearance of intestinal events, complex interpretation of intestinal events and large number of images.

Complex appearance of intestinal events may be due to the motion of the camera in vivo. The camera may be freely moving inside the intestine: forward (in the direction from mouth to anus, e.g. direction 301 marked as "sink"), backward (in the direction from anus to mouth, e.g. direction 302 marked as "source"), and with respect to all three rotational axes marked X, Y, Z. The capsule travels through the small intestine (from the beginning of the small intestine—source, to the end of small intestine—sink) by the small intestine motoric activity, and the gravity. These may be the only two factors that control the capsule's movement, velocity and direction. Generally, the capsule moves forward into the sink, but it is also possible that, for some period of time, the capsule travels backward. Hence, it may be very difficult to determine the exact capsule position or orientation.

Reference is now made to FIG. 3B, which includes several types of in vivo images which may be captured by an imaging capsule. The images may show the lumen hole (complete lumen hole, as shown in images 330, 331, 333, 334) or only a portion of the lumen hole (e.g. as shown in images 332, 335). In some images the intestinal wall may be depicted, e.g. 336 and 337. Moreover, often the field of view of the capsule may be partially or completely occluded by intestinal content (intestinal juices, bubbles and food in digestion, e.g. as shown in exemplary images 338-341).

According to embodiments of the invention, images of movement of intestinal tissue walls may be classified as depicting different categories of intestinal events. In some embodiments, intestinal events may be detected over a sequence of several consecutive image frames. The following categories are examples of intestinal events:

1) "contraction"—movement of intestinal walls and/or lumen;

2) "static closed lumen"—paralyzed or substantially motionless intestine with a closed lumen hole;

3) "tunnel"—paralyzed or substantially motionless intestine with open lumen; and 4) "turbid lumen"—lumen hole and/or wall occluded by intestinal content.

Other categories may be used in addition or instead.

Obtaining a significant amount of image data may allow a detailed analysis of physiological events. However, large amounts of the data may require a long duration of video visualization, and the diagnosis of a study by the physician may take a relatively long time. Detection and characterization of specific events of intestinal motility is known in the area of intestinal motility, such as intestinal contractions detection in "Contraction detection in small bowel from an image sequence of wireless capsule endoscopy" to Vu, H., Echigo, T., et al. (in Proceedings of MICCAI'07; vol. 1.2007, p. 775-783), "Detection of contractions in adaptive transit time of the small bowel from wireless capsule endoscopy videos" to Vu, H., Echigo, T., Sagawa, R., Yagi, K., Shiba, M., Higuchi, K., et al. (Comput Biol Med 2009; 39:16-26), and "Intestinal motility assessment with video capsule endoscopy: automatic annotation of phasic intestinal contractions" to Vilarino, F., Spyridonos, P., Deiorio, F., Vitria, J., Azpiroz, F., Radeva, P. (IEEE Trans Med Imaging 2010; 29(2):246-59).

In "New insight into intestinal motor function via noninvasive endoluminal image analysis" to Malagelada, C., De Iorio, F., Azpiroz, F., Accarino, A., Segui, S., Radeva, P., et al. (Gastroenterology 2008; 135(4):1155-62) and "Functional gut disorders or disordered gut function? small bowel dysmotility evidenced by an original technique" to Malagelada, C., Lorio, F. D., Segui, S., Mendez, S., Drozdzal, M., Vitria, J., et al. (Neurogastroenterology & Motility 2011), the authors have approached the evaluation of motility from wireless capsule endoscopy images. Both methods, first, extract several motility descriptors (each descriptor representing a specific intestinal event) from imaging capsule videos, and second, combine the extracted characteristics to draw a conclusion on small intestine motility. However, as both methods use multidimensional and non linear classifiers, the interpretation of the results by the physicians may be complicated. Moreover, it may be hard to obtain a clear view or perception of what is happening inside the small intestine.

Regarding techniques of in vivo image stream visualization, efforts have been focused on video compaction, e.g. resulting in eliminating or compacting similar frames. For example, in "Evaluating the control of the adaptive display rate for video capsule endoscopy diagnosis" to Vu, H., Sagawa, R., Yagi, Y., Echigo, T., Shiba, M., Higuchi, K., et al. (Proceedings of the 2008 IEEE International Conference on Robotics and Biomimetics IEEE Computer Society. ISBN 978-1-4244-2678-2; 2009, p. 74-79), "Adaptive control of video display for diagnostic assistance by analysis of capsule endoscopic images" to Hai, V., Echigo, T., ohters, (Proc of the ICPR'06; vol. III. 2006, p. 980-983) and "A diagnosis support system for capsule endoscopy" to Yagi, Y., Vu, H., et al. (Inflammopharmacology 2007; 5(2):78-83).

Other methods apply variable sampling rate at acquisition step, e.g. as disclosed in "A model of deformable rings for interpretation of wireless capsule endoscopic videos" to Szczypinski, P. M., Sriram, R. D., Sriram, P. V., Reddy, D. N. (Medical Image Analysis 2009; 13(2):312-324). In this disclosure, the proposed video visualization removes the central part of the frame (e.g. the lumen hole), focusing on the wall visualization. As a result, the presence of the lumen information is not considered in the video visualization. Video compaction, by elimination of the frames of the video depicting sequences in which the capsule is motionless, permits reducing the health professional's review process.

Embodiments of the present invention describe a system and method for displaying motility data, based on analysis and processing of data extracted from image frames captured in the GI tract. Each image frame may be represented as a two-dimensional array of pixels, for example a rectangular or square pixel array of a certain heght and a certain width (e.g., 320×320 pixels). Each pixel may consist of one or more bits of information, representing the brightness of the image at that point and possibly including color information which may be encoded as RGB triples.

Analysis and processing of the image data may be performed automatically by a processing device, without user intervention. The display of motility data, for example using a motility events bar, window or display including for example image strips, cuts or slices, may be performed, e.g., by one or more processors, a workstation, circuitry, a detector or any other computation device. According to some embodiments of the present invention, one or more motility display windows or bars may be displayed to a health professional for diagnosis.

Reference is made to FIG. 1A, which shows a schematic diagram of an in-vivo imaging system according to an embodiment of the present invention. In an exemplary embodiment, the system includes a capsule 40 having one or more imagers 46, for capturing images, one or more illumination sources 42, for illuminating the body lumen, and a transmitter 41, for transmitting image and possibly other information to a receiving device. Typically, the image capture device may correspond to embodiments described in U.S. Pat. No. 7,009,634 to Iddan et al., and/or in U.S Patent Application Publication No. US-2007-0118012 to Gilad, but in alternate embodiments may be other sorts of image capture devices. The images captured by the imager system may be of any suitable shape including for example circular, square, rectangular, octagonal, hexagonal, etc. Typically, located outside the patient's body in one or more locations are an image receiver 12, typically including an antenna or antenna array, an image receiver storage unit 16, a data processor 14, a data processor storage unit 19, and an image monitor or display or visual display unit 18, for displaying, inter alia, images recorded by the capsule 40. Typically, data processor storage unit 19 includes an image database 21.

Typically, data processor 14, data processor storage unit 19 and monitor 18 are part of a personal computer or workstation 11, which includes standard components such as processor 14, a memory, a disk drive, and input-output devices such as a mouse and keyboard, although alternate configurations are possible. Data processor 14 may include any standard data processor, such as a microprocessor, multiprocessor, accelerator board, or any other serial or parallel high performance data processor. Data processor 14, as part of its functionality, may act as a controller controlling the display of the images (e.g., which images, the location of the images among various windows, the timing or duration of display of images, etc.). Image monitor 18 is typically a conventional video display, but may, in addition, be any other device capable of providing image or other data. The image monitor 18 presents image data, typically in the form of still and moving pictures, motility data and in addition may present other information. In an exemplary embodiment, the various categories of information are displayed in windows. A window may be for example a section or area (possibly delineated or bordered) on a display or monitor; other windows may be used. Multiple monitors may be used to display images, motility properties, motility events and other data, for example an image monitor may also be included in image receiver 12.

In operation, imager 46 captures images and may send data representing the images to transmitter 41, which transmits images to image receiver 12 using, for example, electromagnetic radio waves. Image receiver 12 transfers the image data to image receiver storage unit 16. After a certain period of time of data collection, the image data stored in storage unit 16 may be sent to the data processor 14 or the data processor storage unit 19. For example, the image receiver 12 or image receiver storage unit 16 may be taken off the patient's body and connected to the personal computer or workstation which includes the data processor 14 and data processor storage unit 19 via a standard data link, e.g., a serial, parallel, USB, or wireless interface of known construction. The image data is then transferred from the image receiver storage unit 16 to an image database 21 within data processor storage unit 19. Typically, the image stream is stored as a series of images in the image database 21, which may be implemented in a variety of known manners. Data processor 14 may analyze the data and provide the analyzed data to the image monitor 18, where a user views the image data. For example, data processor 14, or another data processor (e.g. in receiver 12) may process images and create a motility bar according to embodiments of the present invention. Data processor 14 operates software that, in conjunction with basic operating software such as an operating system and device drivers, controls the operation of data processor 14. Typically, the software controlling data processor 14 includes code written in the C++ language, and may be implemented using various development platforms such as Microsoft's .NET platform, but may be implemented in a variety of known methods.

The image data recorded and transmitted by the capsule 40 may be digital color image data, although in alternate embodiments other image formats may be used. In an exemplary embodiment, each frame of image data includes 320 rows of 320 pixels each (e.g., 320 rows and 320 columns), each pixel including bytes for color and brightness, according to known methods. For example, each imager pixel may include a color sensor which may correspond to a single primary color, such as red, green, or blue. The brightness of the overall pixel may be recorded by a one byte (i.e., 0-255) brightness value. Images may be stored, for example sequentially, in data processor storage unit 19. The stored data is comprised of one or more pixel properties, including color and brightness. Other image formats may be used.

Data processor storage unit 19 may store a series of images recorded by a capsule 40. The images the capsule 40 records, for example, as it moves through a patient's GI tract may be combined consecutively to form a series of images displayable as an image stream. When viewing the image stream, the user is typically presented with one or more windows on monitor 18; in alternate embodiments multiple windows need not be used and only the image stream may be displayed. In an embodiment where multiple windows are provided, for example, an image window may provide the image stream, or still portions of that image. Another window may include buttons or other controls that may alter the display of the image; for example, stop, play, pause, capture image, step, fast-forward, rewind, or other controls. Such controls may be activated by, for example, a pointing device such as a mouse or trackball. Typically, the image stream may be frozen to view one frame, speeded up, or reversed; sections may be skipped; or any other method for viewing an image may be applied to the image stream.

Data processor 14 may be, include, or may be operationally connected to, a motility display generator 24. For example, processor 14 may execute software or instructions to carry out methods according to embodiments of the invention, including the functionality of motility display generator 24. Motility display generator 24 may process images from the captured set of images, and may obtain visual properties or portions of the images for display in a motility section of the GUI. Motility display generator 24 may produce a motility events bar, based on selected cuts from images in the image stream.

In order to generate the motility events bar, a set of images from the image stream may be provided to motility display generator 24. The set of images may include, for example, all images captured by the imaging device. In some embodiments, a subset of images may be used for generation of a motility events bar. The subset of images may be selected, for example according to different selection criteria.

In one example, a subset of images used for generating a motility events bar may include images captured between certain anatomical landmarks which may be identified in the image stream, e.g. the duodenum, the cecal valve, the Z-line (indicating entrance to the stomach), etc. Two anatomical landmarks may be selected (e.g. may be predetermined in the system, or selected by a user) and all images captured during the time the capsule traveled from a selected anatomical landmark which was captured first to the selected anatomical landmark which was captured later, may be included in the generation of a motility events bar. In another example, images may be selected according to predetermined criteria, e.g. similar to methods described in U.S. Pat. No. 7,986,337 to Davidson et al., which discloses editing methods of an in vivo image stream, to create a shortened movie.
A motility events bar may be generated based on selected images of the shortened movie. In yet another example, images may be merged or fused, e.g. based on similarity between adjacent images, and a motility events bar may be generated based on the subset of fused or merged images. Other image selection methods may be used for determining the subset of image. In some embodiments, different image selection methods may be combined, for producing the subset of images which may be used in the generation of a motility events bar.

In some embodiments, the motility bar may be generated for selected portions of the GI tract. For example, the motility events bar may be generated for selected organs (esophagus, small bowel, colon, stomach, etc.), or for a selected duration of time from the complete imaging procedure (for example, the first 2 hours). According to embodiments of the invention, motility events or motility properties may be detected based on images from an image stream, e.g. selecting image frames or image sequences (e.g. a series of sequential image frames from an image stream, which may include for example a number of consecutive frames selected from the image stream).

Figures 4, 5:
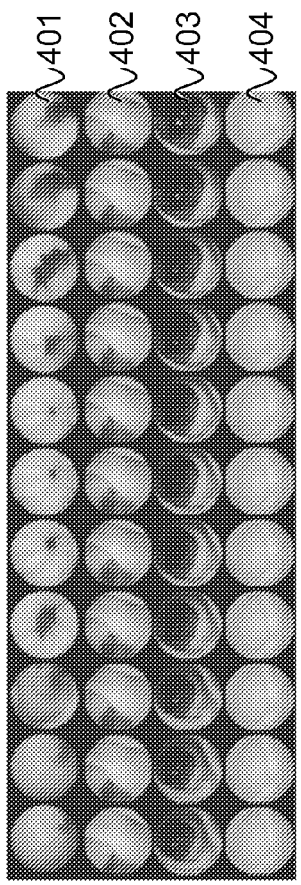
FIG. 4 presents examples of intestinal events captured by the imaging capsule, according to an embodiment of the present invention.
FIG. 5 presents examples of fixed cuts and adaptive cuts according to embodiments of the present invention.

The motility display generator 24 may select, for example, a "strip" from each image of a set of images (e.g. each image in a complete image stream or in a shortened image stream). When used herein, a "strip" of an image may include a cut, a pixel line or a slice of pixels from an image, e.g. one or more adjacent pixels arranged in a line, or one or more lines of pixels which may be obtained or copied from the image. The strip may include, for example, one or more lines of pixels from an image frame. The strip may be selected according to different criteria. For example, a strip may be a "fixed" strip, e.g. a portion of image pixels, the portion being of a fixed size and selected from a predetermined fixed location of the image. A predetermined column of pixels or a predetermined row of pixels may be a fixed strip. For example, line 530 shown in FIG. 5 is an example of a fixed line, e.g. always passing in the same coordinates in each image from the series 501 of images. In some embodiments, a strip may be an "adaptive" strip, e.g. selected from a different position or portion in each image. Each strip selected from an image frame may have different length and/or width or may have a fixed size per image.

Typically, a strip may be selected to run across an image, e.g. from one side of the image to another side. For example, in a round image, two points may be selected on the circumference of the image and the line connecting the points may be the selected strip. In another example, a line may pass through a predetermined point in the image, either at a predetermined (e.g., fixed) angle (which may be measured, for example, between the selected line and a fixed vertical axis in the images) or at a changing angle which may be determined based on image pixel properties. The ends of the strip may correspond to the borders of the image or of a predetermined region of the image which may be used for the motility events bar generation For example, a region of interest may be defined for an image stream, as a fixed template or mask which is selected from each image, based on known optical properties and/or illumination properties of the imaging system.

Different criteria for selection of pixel strips may be chosen by a user (or may be predetermined in, for example, a storage unit or processor), and may be used for generating a motility events bar. In some embodiments, lumen size maximization may be a criterion for selecting a certain strip of pixels from an image. For example, the lumen hole region may appear in different locations in the images, and may not be centered in each image. Different methods for selecting strips may result in different amounts of the lumen hole which is depicted in the selected strip of pixels for each image. According to one embodiment, the strips may be selected to maximize the lumen hole appearance, and thereby maximize the lumen hole appearance in the generated motility events bar.

Similarly, other features which may be detected in GI images and which are of interest to the viewing physician, may be selected as criteria for generating the motility events bar. For example a red area in the images may indicate bleeding, a turbid area may provide indication of the amount of turbid content in the image stream. Other pathological, anatomical or clinically interesting tissue views may be defined. For each defined region of interest in the image (e.g. region depicting red or bleeding area, region including turbid content, region of the lumen hole, region of a detected pathology, etc.), a selection criteria may be predetermined.

The selection criteria may be maximized, or optimized, during the process of selecting pixel strips from the images. Different selected criteria may be combined to generate a motility events bar, and different motility event bars may be generated based on different selected subsets of criteria (and displayed e.g. in parallel or alongside each other). Motility events bars may be generated per user request, according to a specific (selected or predetermined) set of criteria.

A strip may (or may not) be selected to pass through a predetermined point in each image. In some embodiments, the strip may pass through the central point of an image. In other embodiments, a predetermined feature may be detected in each image, and the strip may be selected to pass through the detected feature. For example, a lumen hole may be detected in an image and the strip may be selected to pass through a center of the detected lumen hole, or may be selected such that the lumen length may be maximized in the selected strip. In another example, the predetermined feature may be a pathology which is depicted in an image, e.g. a lesion or polyp. In some embodiments, the user may choose which type of strip is selected from the image to produce a motility events bar.

A combination of different types of strips may be selected, for example from different portions of the image stream. In some embodiments, multiple motility events bars may be produced, based on different strip selection criteria and/or different subsets of image frames used for generating motility events bars. Data processor 14 may include or execute graphics software or hardware to generate a motility events bar. A motility events bar may be generated based on the selected cuts, for example by positioning the cuts adjacently to each other, e.g. in a longitudinal motility events bar or window.

The cuts (or strips) creating the motility events bar may be generated by cutting or copying one or more lines of pixels from each frame of a set of consecutive frames of the image stream. Motility display generator 24 may for example align or position selected strips or pixel lines (typically copies of the strips or pixel lines) adjacently, to form a motility events bar or display.

A strip may be of a certain pixel length and a width of one or more pixels. In some embodiments, the strips may be of a fixed length and width, while in other embodiments the length and/or width of the selected strips may change (for example, based on the type of cut). The length and/or width of the selected strips may be adjusted or resized, e.g. to a predetermined length and/or width, in order to form a motility events bar (e.g., a rectangular bar). The adjustment may be performed by stretching or reducing the strip to a predetermined size (e.g. using interpolation and/or extrapolation methods as known in the art). The bar may further be filtered, e.g. smoothed, to obtain a clearer view of the motility events.

The motility events bar may be used for visualization of motility events which occurred during the imaging procedure, and/or determination of motility properties of the imaged lumen (e.g. may indicate abnormal motility). According to some embodiments, the motility events bar need not be displayed, and may be used (e.g. by a processor) for automatic analysis of the motility events. For example, events may be determined based on the generated motility events bar, and an indication or labeling of event types along the imaging procedure may be displayed to a user (e.g. by motility display generator 24)

Motility display generator 24 and other modules or processes discussed herein may be executed by processor 14 or another processor executing software, and thus in some embodiments processor 14 may include motility display generator 24 or other components or modules discussed herein. Other methods may be used; for example motility display generator 24 may be dedicated hardware or circuitry.

Optionally, motility display generator 24 may detect motility events. Motility events may be related to sequences of images which may have a certain pattern or a specific motility-related property which may be depicted in a sequence of consecutive images from the image stream. For example, an intestinal event may include intestinal contractions, which may be detected as a sequence of images depicting a pattern of an open-closed-open lumen hole. In another example, an intestinal event may include periods of static lumen walls (e.g. repeated imaging of an open lumen hole which may be referred to as an open tunnel sequence) or a closed lumen hole. Another type of intestinal event is a turbid or occluded lumen opening. Other types or categories of events may be detected using images of the image stream.

Intestinal (e.g. motility) events may be detected based on series of consecutive images from the image stream, a motility events bar or window may be generated according to the detected motility events. According to embodiments of the invention, visual detection of defined sequences in video view may be correlated to motility events in the motility event bar. For example, as shown in FIGS. 10A-10H, different types of motility bar displays may be generated based on detected motility events.

Figure 1B:
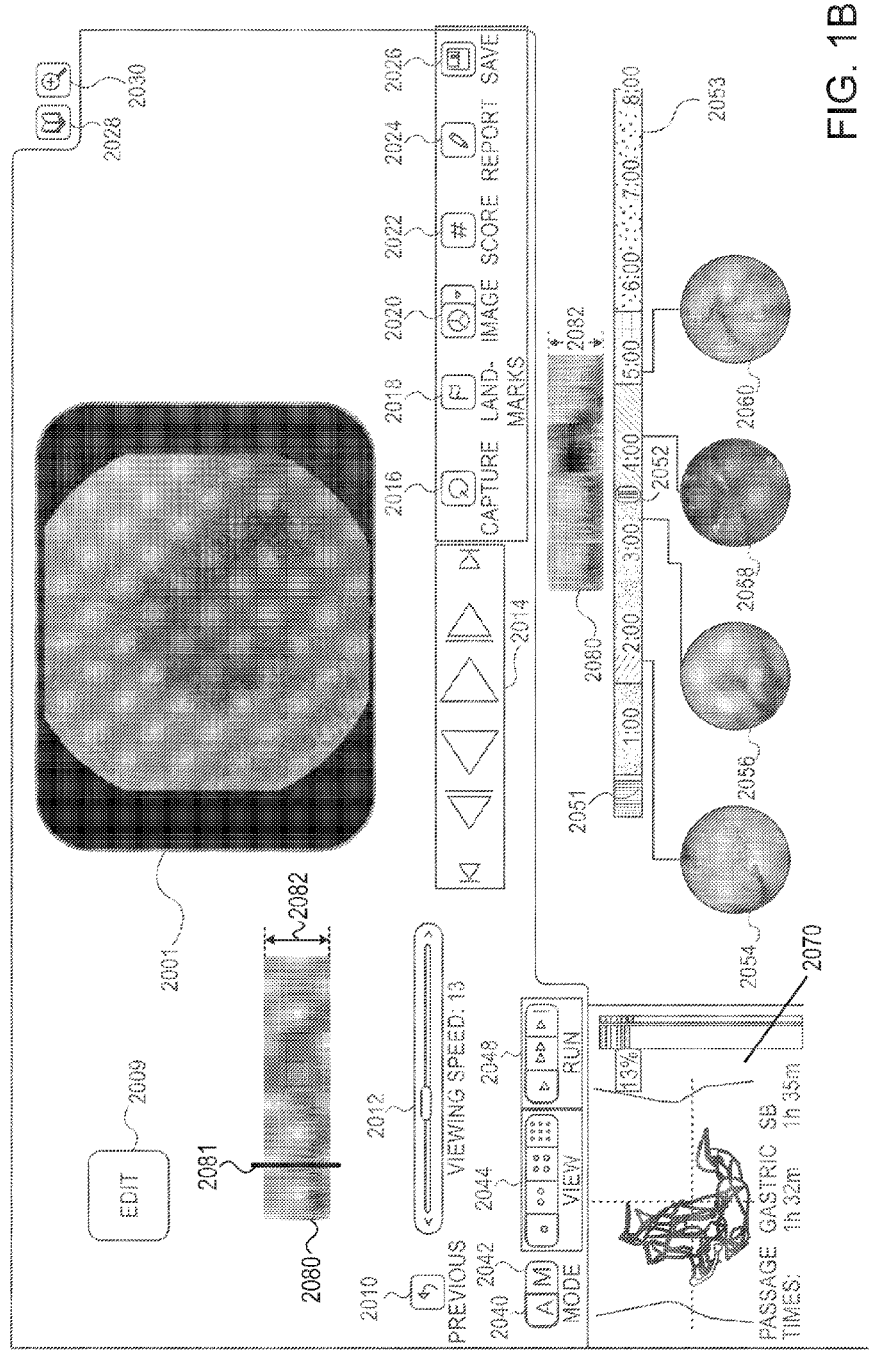
FIG. 1B is a schematic illustration of a Graphic User Interface according to an embodiment of the present invention.

Reference is made to FIG. 1B, which is a schematic illustration of an exemplary Graphic User Interface (GUI) for motility analysis and display of an in vivo image stream captured by an in vivo device. The GUI may include a set of editing tools which may be displayed on a monitor, such as the monitor 18 of FIG. 1A, according to an embodiment of the present invention. One or more image windows 2001 may display images of an image stream, for example a video view of an image stream, which may be a reduced image stream which contains a selected subset of images, or an original (e.g., as captured by the imaging device 40) image stream. In some embodiments, images may be displayed as a set of reduced-size images, e.g. thumbnails or larger images, and not necessarily as an image stream.

Controls 2014 may alter the display of the image stream in one or more image windows 2001. Controls 2014 may include for example stop, play, pause, capture image, step, fast-forward, rewind, or other controls, to freeze, speed up, or reverse the image stream in window 2001. The user may operate controls 2014 using an input device (e.g., input device 22 of FIG. 1A such as a keyboard and/or mouse).

In one embodiment, strips, portions, slices or cuts of images from an image stream, which may be associated with specific criteria, may be summarized or represented in a visual representation of motility events which may be detected in an image stream, for example as shown in motility events bar or display 2080, and may be displayed to the user. The combined strips or cuts may provide an indication of motility events that occurred during the imaging procedure, and the generation of a motility bar or other display may simplify or assist analysis of motility events which occurred during an imaging procedure of the patient's GI tract.

A cursor 2081 may be positioned on the motility events bar 2080, and may indicate to the viewer the correlation between the motility events bar and the image currently being displayed in image window 2001. For example, the strip of pixels obtained from the image frame displayed in window 2001 may be indicated by the cursor 2081. In some embodiments, the time of capture of the image frame may be indicated by the cursor 2081, and the motility events bar may be positioned, for example, alongside the time and tissue color bar 2051. According to some embodiments, the motility events bar 2080 may be displayed separately, e.g. in a different screen, not alongside image stream window 2001, or upon user request.

An edit/create control 2009 may be provided to allow user selection of criteria for generation of a motility events bar 2080, for example, from a list of a plurality of available criteria for selection (e.g., by clicking a tab, check-box, or marker indicating specific criteria). For example, a user may select segments of the GI tract which will be used for producing the motility events bar, or may select different types of motility event bar generation criteria (e.g. maximizing the lumen hole in the generated bar, and/or maximizing other predefined features). The selection of the pixel strip may also be influenced by a user, e.g. by enabling selection of parameters which determine the generated motility events bar, e.g. selecting a fixed cut view and/or adaptive cut views (shown for example in FIGS. 10A and 10B and described in detail herein).

A height 2082 of the motility events may determine the size (e.g. length of the strips). A height 2082 may be set to a predetermined size, or may be created using a user-selectable size bar. According to the determined height 2082 which is to be displayed on the display unit, the length of the selected strips or lines may be adjusted (e.g. resized). For example if the original length of a strip selected from an image is 256 pixels in length, it may be reduced to 128 pixels, 50 pixels, or other number of pixels, according to the determined height 2082. Similarly, if the original length of a selected strip is 120 pixels, and the height 2082 of the motility events bar is set to 256 pixels, the strip may be resized (e.g. stretched) to the length of 256 pixels, for example by duplicating pixels, or by using interpolation or extrapolation methods.

In some embodiments, more than one image stream may be displayed concurrently on the monitor, for example as disclosed in FIGS. 9A, 9B and 10A, 10B of U.S. Pat. No. 7,474,327 to Davidson et al., assigned to the common assignee of the present application and incorporated herein by reference in its entirety. For example, if the imaging device includes more than one imaging system, one or more image streams obtained by an imaging system may be used to generate the motility display. For example, data used in a motility events bar may be summarized from one or more image streams of a single imaging procedure.

Timeline or time bar 2053 may provide a timeline or time chart of the image stream, for example by displaying a line indicating the capture time of images, starting from the beginning of the imaging procedure. A cursor 2052 may be positioned over time bar 2053 and may indicate capture time of an image being displayed, for example, currently in window 2001.

A tissue color bar 2051 may be generated, for example, according to embodiments described in U.S. Pat. No. 8,144,152. Tissue color bar 2051 may overlap with time bar 2053, or may be presented separately. In some embodiments, tissue color bar 2051 may be formed of a number of strips or elements aligned adjacent to each other, or assembled in a continuing bar. Each strip or element in tissue color bar 2051 may represent summarized information, for example, a mean or average color value or intensity, of image frames captured during a predetermined time duration (e.g., a one-minute period). In some embodiments, each strip in the tissue color bar 2051 may correspond to one image frame, e.g. may summarize an average color, intensity, pH level, etc. of a displayed image frame.

Thumbnail images 2054, 2056, 2058 and 2060 may be displayed with reference to an appropriate relative time on the time chart 2053. Related annotations or summaries may include the image capture time of the image corresponding to each thumbnail image, and summary information associated with the respective thumbnail image. A time indicator may provide a representation of the absolute time elapsed for or associated with the current image being shown in image windows 2001, the total length of the edited image stream and/or the original unedited image stream. Absolute time elapsed for the current image being shown may be, for example, the amount of time that elapsed between the moment the imaging device (e.g., capsule 40 of FIG. 1) was first activated or an image receiver (e.g., image receiver 12 of FIG. 1) started receiving transmission from the imaging device and the moment that the current image being displayed was captured or received, or from passage of the in-vivo device of a certain physiological landmark, such as the passage from the stomach to the small intestine. One or more monitors or image windows 2001 may be used to display the image stream and other data.

Different options for displaying motility information to a user are available according to embodiments of the present invention. In one example, motility events bar 2080 may be displayed as a bar at a predetermined location on the display screen, for example aligned with (or alongside) tissue color bar 2051, and/or aligned with (or alongside) time bar 2053. A single cursor indicating the current image being displayed (e.g., indicating the time of capturing the image, and the corresponding pixel strip in the motility events bar) may be used.

In another example, motility events information may be displayed in a separate window or screen, e.g. not alongside the image stream window. The motility events bar 2080 may be displayed upon user demand, for example in a pop-up window which may be presented.

Capsule position window 2070 may include a current position and/or orientation of the imaging device in the gastrointestinal tract of the patient, and may display different segments of the GI tract using different colors. The capsule position may be an approximated or estimated position of the capsule inside the GI tract. A highlighted segment may indicate the position of the imaging device when the currently displayed image (or plurality of images) was captured. A bar or chart in window 2070 may indicate the total path length traveled by the imaging device, and may provide an estimation or calculation of the percentage of the path traveled at the time the presently displayed image was captured.

Buttons 2040 and 2042 may allow the viewer to select between a manual viewing mode, for example an unedited image stream, and an automatically edited viewing mode, in which the user may view only a subset of images from the stream edited according to predetermined criteria. View buttons 2044 allow the viewer to select between viewing the image stream in a single window, or viewing multiple image streams in double, quadruple, or mosaic view mode. The display buttons 2048 may display to the viewer images from the original stream, or only selected images with suspected bleeding indications.

Viewing speed bar 2012 may be adjusted by the user. For example the slider may indicate the number of displayed frames per second. Buttons 2016, 2018, 2020, 2022, 2024, and 2026 may allow a user to capture landmark images or thumbnail images, input a manual score or comment for an image, generate a report for the viewed image stream, and save the clinical findings and markings of the viewer. Control 2028 may allow a user to access a dictionary or atlas of sample images, e.g. of pathologies or anatomical landmarks in the GI tract. Control 2030 may allow resizing the image on display in window 2001 (e.g. zooming in or zooming out).

Reference is now made to FIGS. 2A and 2B, which show different views that can be obtained from the image stream captured by the capsule. Different types of views may be used, for example in combination or separately, for reviewing the image stream: frame view (may include a single frame view as shown FIG. 2A) or a multi-frame view, e.g. several frames displayed at the same timeslot to a user. The frame view may provide information about a specific captured image frame of the intestine (e.g. appearance of lumen hole 220 and tissue wall 230). A video stream view may include streaming, playback, or visual reproduction of the video sequence of image frames. The imaged tissue may be closely examined when reviewing the frame view or video stream view. A schematic illustration of segments of a motility events bar is shown in FIG. 2B. In the motility events bar, motility properties of a desired segment of the video (e.g. lumen wall change over time) may be visualized and analyzed, as may be seen in segments 241, 242, 243.

One way of generating a motility events bar may include obtaining a strip (e.g. a cut or a line) of pixels from each image frame over a sequence of frames, and arranging, aligning or positioning the obtained lines adjacently, according to the capture time, for example in a sequential band or bar. The strip may include a selected fixed portion of each image, e.g. a predetermined fixed strip of pixels selected from each image, the same portion within each image being selected or copied. For example, fixed line 225 may include the pixels that run diagonally across each image of a subset of selected images used for obtaining the motility events bar, e.g. at the same certain position and of the same certain length and angle. In another example the fixed strip may be selected as a line that runs vertically across each image, e.g. from bottom to top. The fixed strip may, in some embodiments, pass through the center point (O in FIG. 2A) of the image.

In some embodiments, the strip may be an adaptive cut, selected or positioned differently in each image. The word adaptive, in this context, means that for each image stream (e.g. video), a processor or computation unit, may search for an optimal cut through each image frame, either in all image frames of the stream or in a selected subset thereof. For each frame, a set of possible cuts may be considered, and the optimal cut may be selected for creating the motility events bar.

In order to determine or select an adaptive strip, a fixed grid or line may be defined for the set of images, for example a vertical line passing through the center of each image frame. The angle measured between the selected pixel strip and the fixed grid may be an adaptive angle (see FIG. 6A), and may be selected in each image frame according to predetermined criteria.

One example of an adaptive cut may be selecting a strip passing through a region of a lumen hole which may be detected in the image, or according to an estimation of a lumen hole in the image, e.g. the strip that runs through a center of the detected lumen hole area in the image. The lumen hole may appear in different regions of different images, e.g. due to the imaging device rotation during the imaging procedure. Methods for detection of a lumen hole are disclosed, for example, in FIG. 2 of U.S. Pat. No. 8,335,362, which is assigned to the common assignee of the present application and incorporated by reference herein in its entirety.

The length of the line or strip selected from image frames may vary, and may depend on the line selection method and/or on the size of the image used for obtaining the strip or line. For example, a vertical line running through the center of a square image of width 320 pixels and height 320 pixels, will be 320 pixels in length (and may be, for example, one pixel in width). A diagonal line passing through the center of the same image will be of about 452 pixels in length. When selecting a line or strip that passes through a dynamically detected area (or point) in the image, and/or using a dynamic angle selection for determining the angle at which the line passes in relation to the vertical and horizontal lines passing through the center of the image, the length of the line may change for each different line selection. Furthermore, the images used for obtaining a motility events bar may have a different shape than a square, e.g. may be circular or rectangular and may have rounded corners. Therefore, in some embodiments, the length of the lines may require normalization to a predetermined value, e.g. to the selected height 2082 of the motility events bar 2080. Similarly, the width of the line selected from image frames may vary in some embodiments, and may be normalized or cropped to a predetermined or user-selectable size.

FIG. 4 presents examples of four types of intestinal events captured by the imaging capsule. The events include sequences of consecutive images captured by the capsule 40. As may be observed, the contraction pattern is determined when an open-closed-open lumen hole pattern is visible, for example in contraction sequence 401. When no movement of intestinal wall (and/or lumen) is visible, the intestine is substantially motionless and the capsule is "paralyzed" inside the intestine, as may be seen in static closed lumen sequence 402. The lumen hole depicted in images of this sequence is substantially closed, therefore the sequence may be categorized as a static closed lumen sequence. When the intestine is generally motionless and the lumen hole is (substantially) open, a tunnel sequence 403 may be determined. When the captured images include mostly turbid intestinal content, which occludes or blocks the tissue depicted in the image, the sequence may be determined as a turbid lumen sequence 404.

According to embodiments of the invention, intestinal movement patterns may be determined based on a motility events bar. The change in the intestinal movement patterns (e.g. the sequence of motility events detected in an in vivo image stream) may be an indicator of motility properties of a patient's GI tract, e.g. an indicator of normal intestinal activity or a motility disorder.

Due to the free movement of the capsule inside the intestine, an image of the lumen hole is not always captured in the center of the image frame. A straight-forward approach may include selecting a fixed cut, e.g. including a straight line of pixels passing through a fixed coordinate in the frame (e.g. a line running through the center of the frame) may not be an optimal selection for presentation of motility information. For example, a fixed cut is shown in the sequence of images 501 of FIG. 5. The fixed cut 530 runs vertically through the center of the frame, in each image, for all images used for generation of the motility events bar.

A method for visualization of in vivo image streams may include motility events bar based on adaptive image cut. The motility events bar based on adaptive image cut may include a bar generated of a series of cuts through the in vivo images to produce a motility events bar of intestinal events. Different positions and sequences of cuts may be selected to generate different representations of the intestinal motility, the sequences of cuts being through consecutive frames of the image stream. The adaptive cut method may be based on an optimization problem that maximizes the probability of the selected line in each frame passing through image portion showing lumen hole. An example of adaptive cut through a sequence of images is shown in FIG. 5, row 502. The adaptive cut may include a straight line, which may be selected to pass through a specific point in each image, e.g. the center of the image. The adaptive cut may be selected differently in each image, based on the position of the lumen hole (e.g., if it is visible in the image).

Presenting a motility events bar reduces the amount of information provided by the original image stream (or a subset thereof) captured by the capsule 40, since it presents a summarized view of the video sequence in a two-dimensional bar. The motility events bar may permit simplified evaluation (e.g. by an expert) of the intestinal motility in a quick view. Using the adaptive cut method, the motility information presented may maintain, where possible, the lumen and/or tissue wall information of the patient's GI tract, and thus may increase the likelihood that the selction of image data for generating the motility events bar is optimal for analysis of motility events or motility properties of an image stream.

Defining or selecting an optimal cut in an image frame may be determined according to different criteria and conditions. The criteria may include, but is not limited to, one or more of the following: maximizing visibility of one or more features depicted in the image frames, and maintaining smoothness of the generated motility events bar. The criteria may be predetermined, for example stored in a storage unit which may be operationally connected to a processing unit (which may be used for determining an optimal cut in an image frame), or may be selected by a user, for example from a list of available criteria.

Figure 6A:
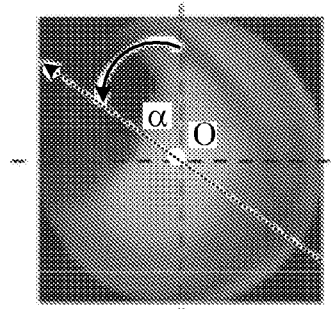
FIG. 6A shows an exemplary cut through an in vivo image i, at a denoted angle, according to embodiments of the present invention.
Figure 6B:
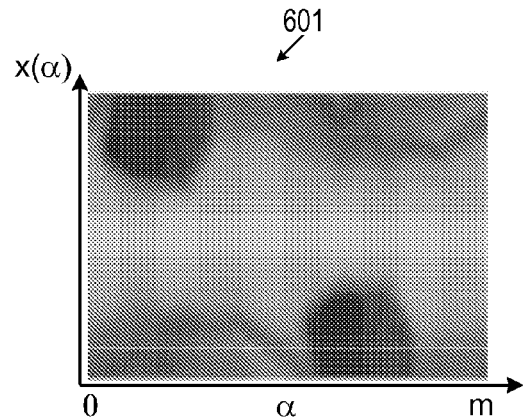
FIG. 6B shows all possible cuts through the image i, according to embodiments of the present invention.

The in vivo image stream may be seen as a series of n consecutive image frames. The n frames may be the total number of frames of the image stream (or subset thereof) used for generating the motility events bar. In one embodiment, adaptive cuts may be selected to pass through a predetermined point O (e.g. center of the image). Each frame i may have m possible adaptive cuts αi Ω={1, . . . , m}. The angle αi denotes the angle between the vertical line passing thorough the center of the frame and the line representing the cut, as shown in FIG. 6A. FIG. 6B shows a set of possible cuts through the image i, according to different selected angles αi. The angle αi is shown on the x-axis of graph 601, and the selected cut of pixels which corresponds to the selected angle is shown on the y-axis of graph 601.

Figure 6C:
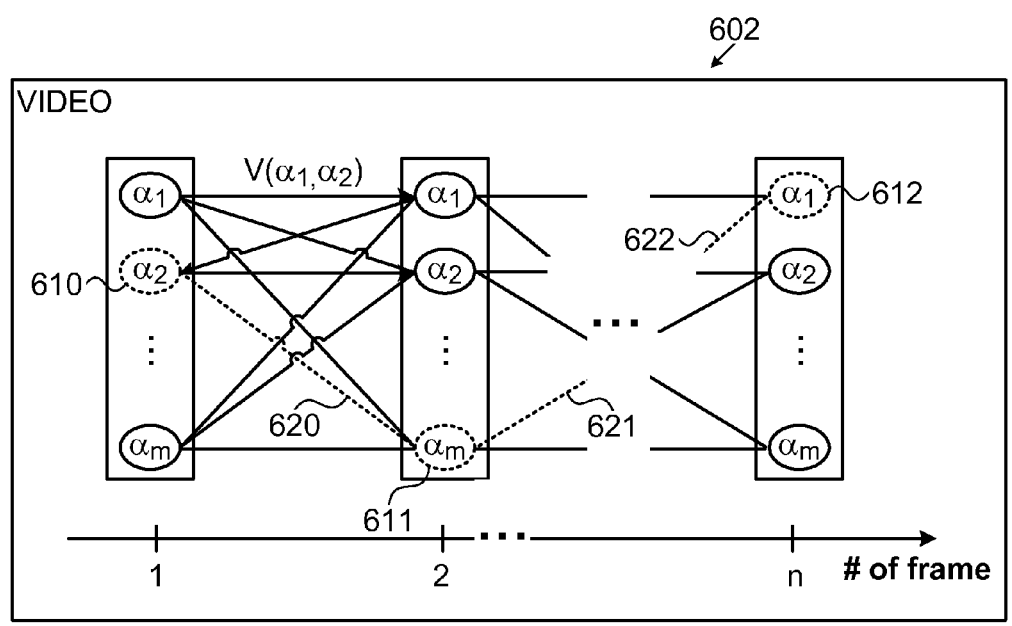
FIG. 6C shows an optimal path selected from possible paths in a graph according to embodiments of the present invention.

Graph 602 shown in FIG. 6C includes n frames (represented by n groups of nodes). For each frame i, there are m nodes which represent possible selections of the angle $\alpha_i$. The cost of passing from cut $\alpha_i$ in frame i to cut $\alpha_{i+1}$ in frame (i+1) may be denoted as V ($\alpha_i$, $\alpha_{i+1}$). Constructing an adaptive motility events bar may be approached as an optimization problem, wherein a set of constraints should be preserved. For example, the set of constraints may include two constraints: the lumen hole visibility, and the smoothness of the view. Other constraints or criteria may be determined.

The lumen hole visibility constraint may ensure that the cut passes through the lumen hole, while the smoothness constraint may be important to maintain the continuity and interpretability of the view and to control the velocity of changes between different angles of cuts, e.g. in sequential image frames. If the velocity of changes between different angles of cuts is too fast, the resulting motility events bar may be less interperable, since the changes between adjacent strips of the bar may be too big, thus motility events may be less visible or less detectable. This task may be reformulated as the problem of finding an optimal path, e.g. as presented by nodes 610, 611 and 612 connected by arcs 620, 621 and 622 in graph 602. The cost of a candidate solution ($\alpha_1$, . . . , $\alpha_n$) to the problem can be defined, for example, according to the following cost equation:

$$E(\alpha_1, \ldots, \alpha_n) = \sum_{i=1}^{n} D(\alpha_i) + \sum_{i=2}^{n} V(\alpha_{i-1}, \alpha_i) \quad (1)$$

The terms $D(\alpha_i)$ are used to ensure that the cut in the ith image passes through the lumen hole, while the $V(\alpha_{i-1}, \alpha_i)$ ensures that the cuts $\alpha_{i-1}$ and $\alpha_i$ are compatible (this term captures the cost of change between two consecutive frames, i−1 and i). The best solution may be the one that passes through all video frames and has the minimal cost.

Due to the large amount of frames in a GI image stream, (n may be up to, for example, 60,000 frames or a different number of frames), Dynamic Programming (DP) may be used in order to find the minimum of the function described by Eq. (1), and to obtain the angles for the cuts in the adaptive motility events bar generated for an image stream.

DP may be used in discrete optimization problems. The DP finds the global optimum to the given problem. The basic idea of DP is to decompose a problem into a set of subproblems, where the original solution can be quickly solved and the subproblems can be efficiently solved in recursive way (as disclosed, for example, in "Dynamic programming and graph algorithms in computer vision" to Felzenszwalb, P. F., Zabih, R., IEEE Transactions on Pattern Analysis and Machine Intelligence 2011; 33:721-740. Hence, the difference with respect to the classical recursive methods is the memozation (storing the solutions to already solved subproblems).

Let the table $B(\alpha_i)$ denote the cost of the best assignment of angle cuts to the elements from 1 to i, with the constraint that ith element has label $\alpha_i$. The size of the table B is n×m, where m denotes the cardinality of the set Ω, and n denotes the number of frames. The table $B(\alpha_i)$ may be filled in increasing i, e.g. by using the following recursive equations (other equations may be used):

$$B(\alpha_1) = D(\alpha_1),$$

$$B(\alpha_i) = D(\alpha_i) + \min_{\alpha_{i-1}}(B(\alpha_{i-1}) + V(\alpha_{i-1}, \alpha_i)) \quad (2)$$

The subproblems may be defined as: for the first frame, $B(\alpha_1)$ is the cost of assigning the angle $D(\alpha_1)$ to the first frame. For every other frame, $B(\alpha_i)$ is the cost of assigning the angle $D(\alpha_i)$ plus the minimal transition cost from i−1 to ith frame $\min\alpha_{i-1}(B(\alpha_{i-1})+V(\alpha_{i-1},\alpha_i))$. At each iteration of the algorithm, a vector D of size 1×m and a matrix V of size m×m are calculated.

In order to avoid recalculating the solutions to subproblems, a matrix T is being filled in while calculating the tables $B(\alpha_i)$. The T matrix may store optimal solutions to subproblems, thereby enabling reduction of the calculation amount, each subproblem being calculated only once. Each row of the matrix has a size of m and stores the best way to get to the ith solution from the (i−1)th solution. Each time a new value is added to the $B(\alpha_i)$, the matrix T is updated according to the rule:

$$T(\alpha_i) = \operatorname*{argmin}_{\alpha_{i-1}}(B(\alpha_{i-1}) + V(\alpha_{i-1}, \alpha_i)) \quad (3)$$

As a result, the matrix T stores the indices of nodes through which the algorithm should pass in order to get the optimal solution to the problem. Finally, the overall solution is tracked back $\alpha_{i-1} = T(\alpha_i)$ starting at i=n. As a result, the sequence of optimal cuts ($\alpha_i$, . . . , $\alpha_n$) through, for example, all frames in the image stream, may be obtained. This sequence of optimal cuts can be seen as the path of minimal cost through the frames in the image stream. In some embodiments, applying the smoothing term may reduce blob detection rate.

The lumen in the images captured by the imaging capsule is often seen as a dark region or blob, usually surrounded by the intestinal wall. The image cut that passes through the intestinal lumen hole can be characterized in terms of mean and variance of the color intensity. More than one cut or strip may pass through the lumen hole. In order to ensure the lumen hole visibility (in the generated motility events bar), a method may include searching for the cut of high variance and low mean value (where mean and variance are calculated using the pixels that compose the strip or cut). High variance $\sigma^2$ assures that the cut preserves maximal information of the frame maintaining, where possible, the lumen and/or wall information. Low mean value μ assures that the cut passes through the dark area of the image. The dark area of the image, with high probability, may depict a lumen hole.

Let $x(\alpha_i)$ denote the vector of the pixels from the image cut localized in the angle $\alpha_i$ and passing through the center of the image, e.g. as shown in FIG. 6A. The lumen hole visibility cost D may be defined as follows:

$$D(\alpha_i) = 1/(\sigma(x(\alpha_i))+1) + \mu(x(\alpha_i)) \quad (4)$$

It is assumed that the values of the vector $x(\alpha_i)$ are in the range of [0, 1].

In order to assure smoothness of the motility events bar, a term that controls the changes between the angles of the consecutive frames may be calculated. The smoothness may be restricted by two factors: angle change $V^1(\alpha_{i-1}, \alpha_i) = 180° - |180° - |\alpha_{i-1}, \alpha_i||$, and similarity between two consecutive cuts $V^2(\alpha_{i-1}, \alpha_i) = \|x(\alpha_{i-1}) - x(\alpha_i)\|_2$. The final smoothness term V may be defined, for example, using the following equation (other equations or calculations may be used):

$$V(\alpha_{i-1},\alpha_i) = \beta(V^1(\alpha_{i-1},\alpha_i)/\gamma_1)^2 + (1-\beta)(V^2(\alpha_{i-1},\alpha_i)/\gamma_2)^2 \quad (5)$$

where quadratic term in $V^1$ and $V^2$ is introduced in order to penalize the sudden changes, $\gamma_1$ and $\gamma_2$ normalization terms, and $\beta$ [0, 1] is a parameter controlling the weight of change of angles and similarity of cuts in consecutive frames.

Let m denote the number of possible cuts and n denote the number of frames. The method may include, at each iteration, calculating:

1) m means of pixels in cut;
2) m variances of pixels in cut;
3) $m^2$ angle differences between cuts in consecutive frames and
4) $m^2$ similarities between cuts in consecutive frames.

The computational complexity of the algorithm is $O(m^2 n)$.

This embodiment was tested on synthetic data and on image data captured by an imaging capsule. The image data was obtained using the PillCam® SB2 capsule endoscopy camera developed by Given Imaging, Ltd., Israel.

During the validation three types of cuts for motility events bar were tested:

1. (Acut)—The adaptive cut described herein,
2. (Acut-)—modification of the adaptive cut embodiment, obtained by removing smoothing term V. In the Acut– embodiment, Eq. (1) transforms to:

$$E(\alpha_1, \ldots, \alpha_n) = \Sigma_{i=1}^n D(\alpha_i),$$

in order to assess the influence of the smoothness term V in the energy (cost) function.

3. (Fcut)—Longitudinal view with fixed cut.

Reference is now made to FIGS. 7A-7D, which show examples of synthetic data which was generated for testing a display and analysis method according to an embodiment of the present invention. In an experiment using synthetic data, a synthetic video of 40,000 frames was created, using a frame capture rate of 2 frames per second. On a uniform background, a dark blob was placed. The blob position and blob size were changed on consecutive frames depending on the intestinal event. The following intestinal events have been used to create the synthetic video: tunnel, static, contraction, undefined movement. In order to make the video more realistic, the events order and duration have been defined with random number generator. The presence of turbid content occludes the lumen and changes the color of the frame from pink-orange to green-brown. In order to keep the experiment simple and interpretable, turbid sequences were not considered. The following definitions of specific intestinal events may be used to generate image sequences: tunnel, static, contractions and undefined movement.

Figures 7A, 7B, 7C, 7D, 8:
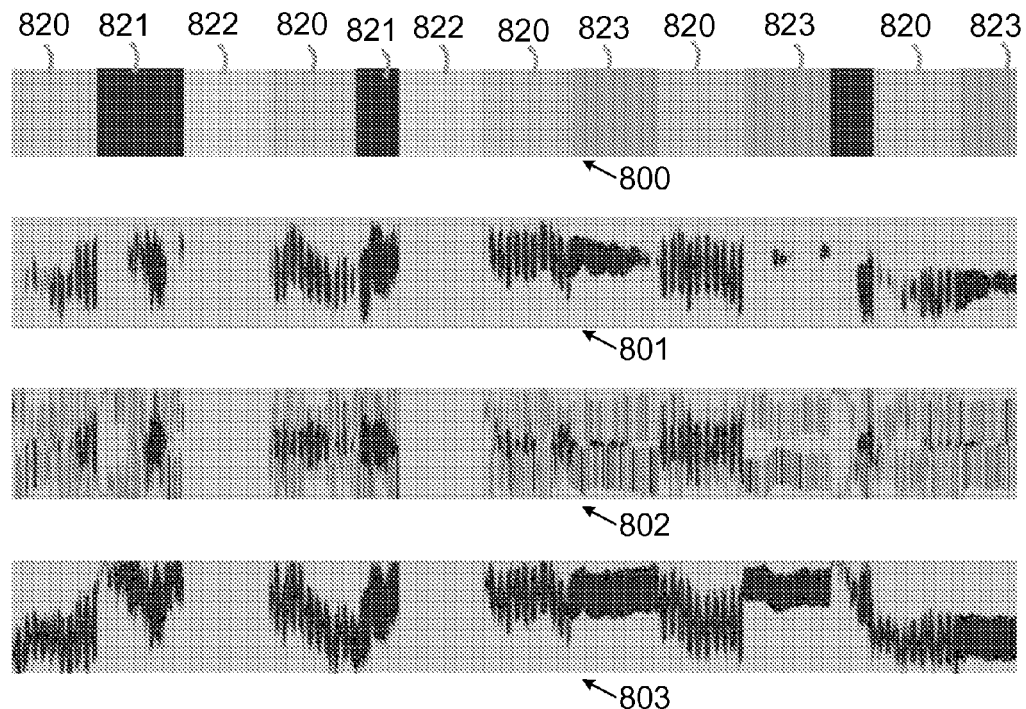
FIGS. 7A-7D present examples of synthetically created intestinal events according to embodiments of the present invention.
FIG. 8 presents examples of motility events bars generated according to embodiments of the present invention.

An example of a tunnel sequence is presented in FIG. 7A. A tunnel sequence is defined as a sequence of paralyzed (e.g. still or substantially unmoving) intestine with an open lumen hole. Lumen hole size in a tunnel sequence is defined as highly constant (e.g., ±2 pixels difference in diameter between two consecutive frames—other numbers of pixels may be used) and substantially open (larger than, e.g., 70 pixels in diameter).

An example of a static sequence is presented on FIG. 7B. A static sequence is defined as a sequence of paralyzed intestine with closed lumen hole (e.g. no lumen hole or a small lumen hole may be observed in the frame).

An example of a contraction sequence is presented on FIG. 7C. A contraction sequence is defined as a sequence of frames with the presence of intestinal contraction, which is detected as a substantially symmetric pattern of open-close-open lumen with duration of, for example 9 frames (more or less frames may be used), and a fixed frequency of, for example, 6 contractions per minute (other numbers may be used). The lumen size of the central frame of the intestinal contraction is defined as 10% of the initial lumen size.

An example of an undefined movement sequence is presented on FIG. 7D. An undefined movement sequence is defined as an irregular movement of the lumen hole size (e.g., ±30 pixels variation between consecutive frames) and the imaging capsule (±30 pixels variation between consecutive frames).

FIG. 8 shows examples of longitudinal view bars generated from synthetic data, and obtained using different cuts. Bar 800 represents the ground truth, which is determined according to the following segments of the bar: contraction sequences 820, undefined movement sequences 821, static sequences 822, tunnel sequences 823. Bar 801 displays the generated Fcut, bar 802 displays the generated Acut—and bar 803 displays the generated Acut.

Video segmentation may include, for example, visual detection of one or more of the following sequences: static, turbid, tunnel, contractions or undefined. Other sequence types or categories may be used. In this context the detection may include, for example, marking the beginning and the end of each type of sequence, or correlating a start image and an end image from the image stream to each type of sequence. In another example, images in the image stream may be categorized or attributed as belonging to one or more types of event sequences.

FIGS. 10A-10H show examples of applying Acut and Fcut to image streams captured by a capsule. The lumen hole visible in the motility events bar may be larger in the view obtained using the Acut method as shown in FIGS. 10A, 10C, 10E and 10G, compared to the view obtained using the Fcut method, which is shown in FIGS. 10B, 10D, 10F and 10H.

Figure 11:
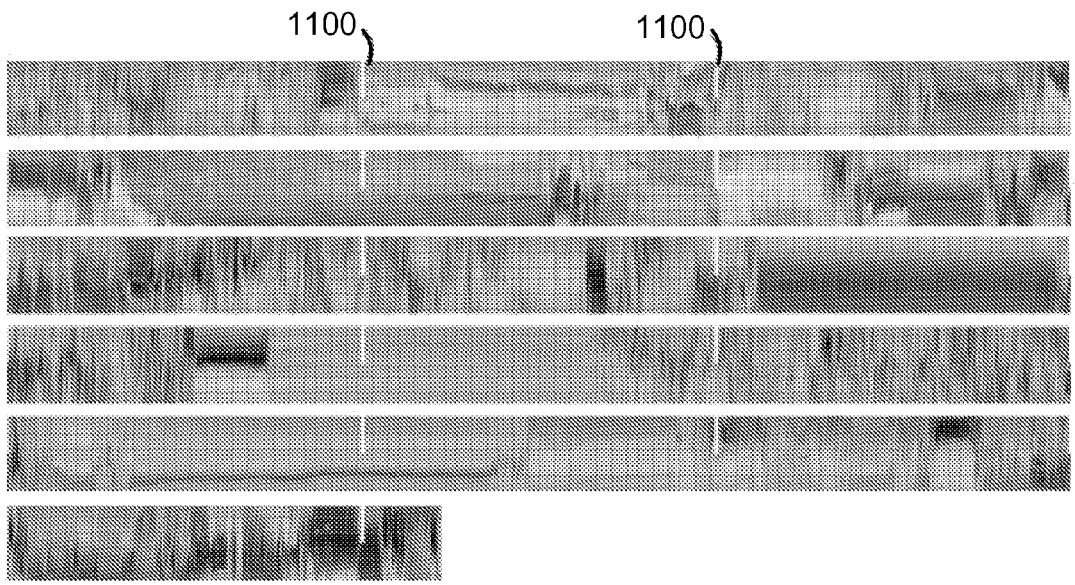
FIG. 11 presents an example of a motility events bar generated for an in vivo image stream according to embodiments of the present invention.

An example of an Acut motility events bar is shown in FIG. 11. The bar represents data of the complete small intestine, e.g. from duodenum to cecum. Each white stripe 1100 may indicate a portion of the video which equals, for example, 10 minutes of the video duration. The Acut motility events bar and the original image stream (using GUI as shown, for example, in FIG. 1B) may be presented to a health professional, for marking a beginning time and an end time of the motility-related sequences such as: tunnel, static, contraction, turbid and undefined movement.

Figures 9A, 9B, 9C, 9D, 9E, 9F, 9G, 9H:
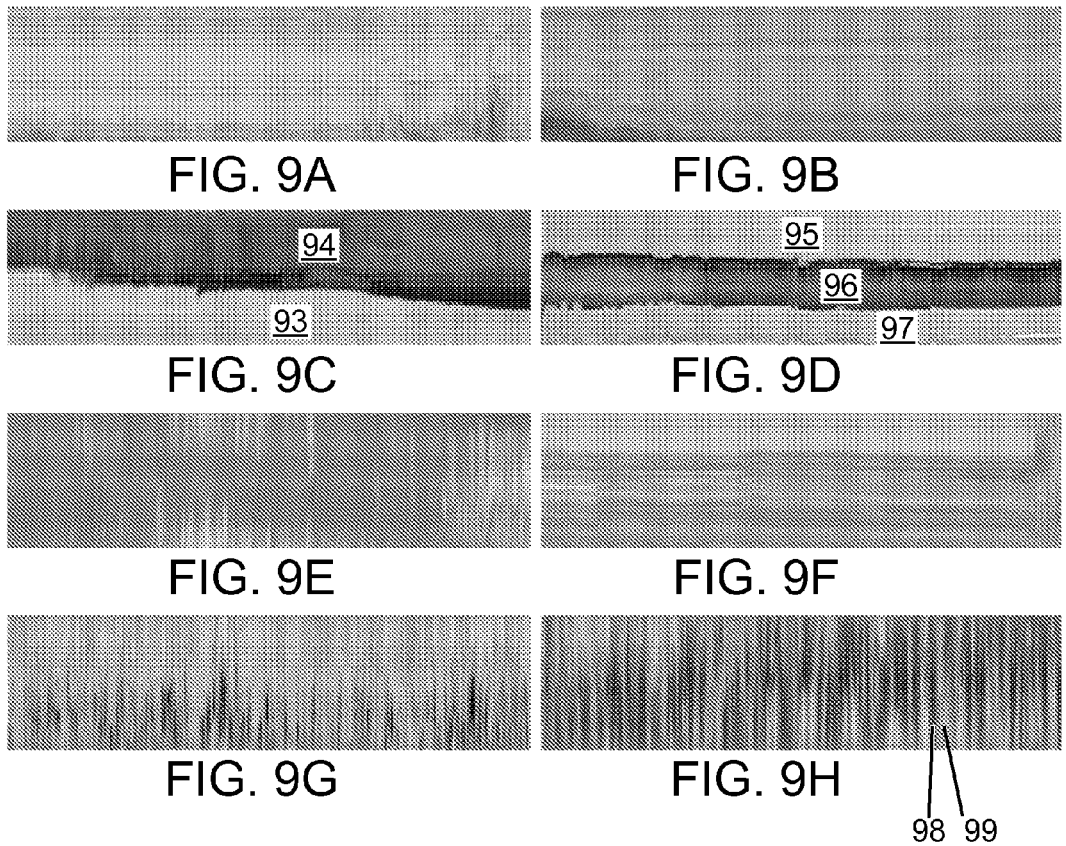
FIGS. 9A-9H present examples of motility events bars representing different intestinal events, according to embodiments of the present invention.

Examples of event sequences which may be emphasized when viewing a motility events bar obtained using Acut is shown in FIGS. 9A-9H. FIGS. 9A and 9B show a static event of the imaged GI tract. The uniform (or homogeneous) texture of the events bar portion shown in FIGS. 9A and 9B indicates that there were no substantial changes between sequential images which are represented in these events bars. Therefore, it is possible to identify the represented portion of the image stream shown in these bars as a static event, e.g. a period of time during which the capsule was substantially positioned in the same location in the GI tract.

FIGS. 9C and 9D show examples of tunnel events. The dark portion 94 of the events bar in Fig, 9C indicates the lumen hole in the represented images. Since the dark portion 94 and lighter portion 93 are substantially uniform along the events bar portion which is shown in FIG. 9C, it may be inferred (e.g. by the professional who is reviewing the image stream or automatically by a processing unit such as processor 14 and/or motility display generator 24, using image processing techniques), that the lumen hole which is indicated by dark portion 94 is substantially open along the GI tract portion which is represented by the events bar of FIG. 9C. Similarly, dark portion 96 indicates the lumen hole in the events bar of FIG. 9D, while lighter portions 95, 97 indicate the tissue wall imaged in the GI tract portion which is represented by the events bar of FIG. 9D. The lumen hole portion 96 and the tissue wall portions 95, 97 remain substantially uniform in size and position along the events bar.

FIGS. 9E and 9F show examples of turbid sequences. Turbid sequences may be defined when the images captured in the corresponding portion of the GI tract include at least a certain level of intestinal content, bubbles, food remains, etc. The level of turbid content indicated as a turbid sequence in the image stream may be predefined and stored in a storage unit, e.g. storage 19. Turbid sequences may be identified in the image stream by using the events bar, (e.g. by a health professional or automatically by a processing unit). For example, if the color of the sequence in the events bar is greenish or brownish, the sequence of images may be defined as a turbid sequence.

A variety in contraction rhythm may be noted in different contraction sequences, e.g. in FIGS. 9G and 9H. Both FIGS. 9G and 9H show sequences of images with rapidly changing scenery. The change in scenery is indicated by a detectable difference between adjacent lines in the events bar. Contractions may be identified in the events bar when the dark portions (corresponding to the lumen hole in the captured images) and lighter portions (corresponding to tissue wall in the captured images) of a line of pixels in the events bar interchange between adjacent lines. For example, in FIG. 9H, vertical pixel line 98, includes mostly a dark portion (the pixel line is substantially dark). The adjacent pixel line 99 includes mostly a light portion. Such interchanging texture suggests that the body lumen was widely open when the images corresponding to pixel line 98 were captured, and substantially closed when the images corresponding to pixel line 99 were captured. When a sequence of interchanging texture is detected in the events bar, the sequence may be defined as a contraction sequence, e.g. the corresponding portion of the image stream captures contractile activity of the GI tract.

A health professional such as a doctor or nurse, may label several types (e.g. five types) of event sequences using a video view. In addition, the health professional may label the sequences using a motility events bar (e.g., Acut). When comparing labeling or annotation durations of the health professional in both display methods, the motility events bar may be advantageous, for example may substantially reduce the review time (for detection of motility-related events).

According to some embodiments, the analysis of motility data may be performed by a processor which generates a motility data bar. For example, the following motility-related data may be identified (e.g. automatically detected by a processor) based on the motility events bar:
  frequency and/or number of intestinal contractions;
  duration or average duration of contraction sequences;
  frequency, number, duration or average duration of tunnel sequences;
  frequency, number, duration or average duration of turbid sequences;
  frequency, number, duration or average duration of static closed lumen;

An indication and/or calculation of detected motility events may be provided, along with a range of normal behavior or abnormal behavior for the detected motility parameter. The range may be provided as reference to the user, e.g. the normal number of contractions in a specific organ or within a predetermined time duration may be displayed along with the detected number of contractions in the analyzed image stream. An indication of normal or abnormal behavior may be provided based on comparison.

A processor may identify single events and may display an indication of the events to a user. The analysis of events and/or motility-related parameters may be performed for a certain region (or a plurality of regions) or a segment of the image stream, for a subset of images from the image stream, or for the whole image stream. A method for construction of a motility bar for motility analysis is presented according to an embodiment of the invention. The method may adapt a frame cut angle to the lumen position by minimization of a cost function. This problem formulation may allow applying Dynamic Programming to efficiently find the global minimum to the proposed cost function. Experimental results on synthetic data and in vivo image streams show that embodiments of the invention may preserve lumen hole and/or wall separation, and expert annotations may coincide well with the ones obtained using video view. Moreover, time required for visual inspection may be much faster, e.g. four time faster, using motility bar compared to video stream view.

Using the motility events bars according to embodiments of this invention may make different motility events more visible, and may assist in simplifying motility analysis. Furthermore, the method may allow analysis, for example automatic analysis, of different contractile rhythms and/or patterns (e.g. different frequency, duration and number of occurrences of motility event sequences). Interesting motility phenomena may be emphasized in the motility events bar, for example: regular intestinal contraction with the frequency of 11 contractions per minute, irregular mixing contractions (e.g. contractions responsible for food mixing) and one-minute-cycles (e.g., every minute the intestine changes its state, repeating a pattern: paralyzed intestine—contractile movement). Other patterns and/or rhythms of motility events may be detected, analyzed and/or presented to a user according to embodiments of the invention.

Figure 12:
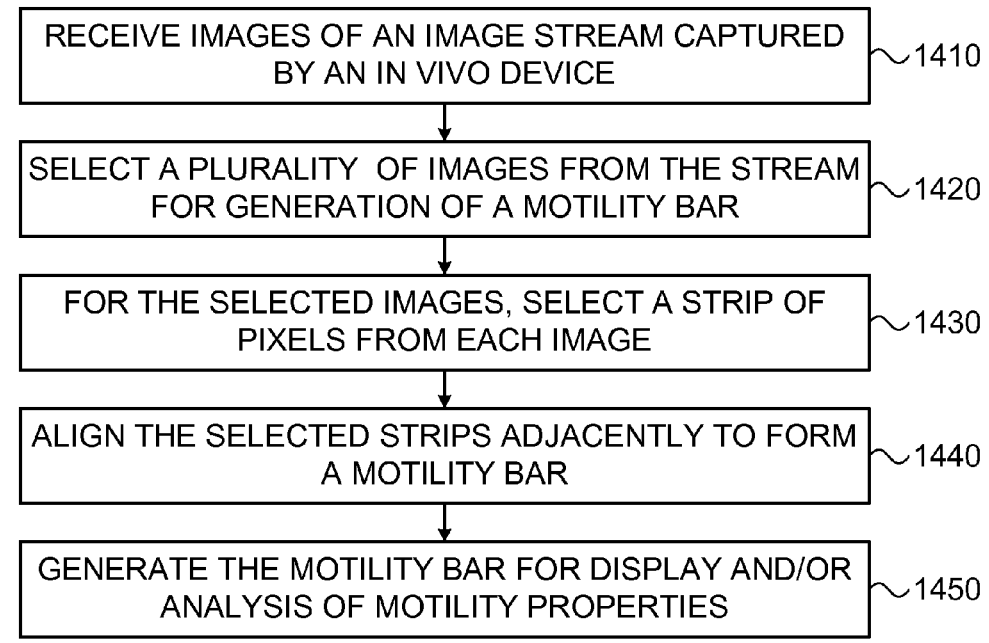
FIG. 12 is a flowchart of a method for generating and displaying a motility events bar based on an in vivo image stream, according to embodiments of the present invention.

Reference is now made to FIG. 12, which is a flow chart of a method for generating a motility events bar based on an in vivo image stream, according to embodiments of the present invention. In operation 1410, images of an image stream captured by an in vivo imaging device may be received, for example in a workstation such as workstation 11 or a receiving unit such as receiver 12. The image stream may include in vivo images captured sequentially over a period of time by an in vivo imaging capsule (e.g. capsule 40), and may be stored in a storage unit such as storage 19 or storage 16. The images may be processed, e.g. by a processing unit (for example processor 14). Each image may be represented as a two-dimensional array of pixels, for example a rectangular or square pixel array of 320×320 pixels. Each pixel may contain a value corresponding to a primary color, e.g. red, green or blue.

In optional operation 1420, a plurality of images may be selected from the captured image stream, and the selected images may be used for generation of a motility events bar. In one embodiment, all images of the image stream may be used (i.e., all images may be selected) while other embodiments allow selecting a subset of images from the complete set of images captured by the imaging device. The method may include selecting a subset of images from the image stream according to certain criteria, for example selecting certain segments or portions of the image stream for producing a motility events bar, while other segments may not be selected. For example, sequences of images captured in certain organs of the GI tract may be selected. In one example, only images captured in the small bowel may be used for generating the motility events bar. Other portions or segments of the image stream may be selected. Images which are blurred, too bright or too dark may not be selected.

Typically, the selected images may include a plurality of sequential images (e.g. consecutive image frames captured sequentially by the imaging device), in order to maintain smoothness of the generated motility events bar and to better emphasize intestinal events or intestinal features in the image stream.

In operation 1430, a strip or line of pixels may be selected from each image of a plurality of images selected from the image stream (e.g., a subset of images). Different criteria for selecting the strip may be determined (e.g. by a user, or predetermined). The strip may be selected as a fixed cut or an adaptive cut. For example, a linear array of adjacent pixels may be selected. The strip or line of pixels need not be oriented parallel to a row or column of pixels, but may be oriented at another angle to a row or column; e.g., the strip or line may be diagonal.

The selected strip of pixels may include, for example, a line of pixels selected from an image. In some embodiments, the strip may be a straight line of pixels. The strip may be a fixed strip or cut, e.g. pixels located in the same coordinates in the image pixel array may be selected from each image. For example, if the image include an array of 256 horizontal rows of pixels and 256 vertical columns of pixels, the selected strip may include all pixels in the central column of the pixel array (e.g. column 128). More than one line of pixels may be selected in the strip, for example two or more adjacent columns (e.g. columns 127, 128 and 129 in the example of 256×256 pixels). The selected strip may pass through a predetermined point in the image. In one embodiment, the predetermined point may be a central point in the image (e.g. the center of the pixel array). Other predetermined points may be selected.

In some embodiments, the strip may be an adaptive line of pixels selected from an image. For example, the line may not necessarily pass at the same position in the images selected for producing the motility events bar, and instead the line position, orientation or other characteristics may be selected for each image according to certain features or properties of the image. For example, a certain feature or property may be detected in the image (e.g. a dark lumen hole or a blob, a bright portion of the image, etc.). The strip may be selected to pass through the detected feature or portion of the image, for example through a central point or the center of gravity of the detected feature. In some embodiments, the adaptive strip may pass through a predetermined point in the image (e.g., a central point or pixel in the pixel array), and different angles may be determined for selecting the strip in each image. Other embodiments allow selecting lines that do not pass through a predetermined (e.g. fixed) point in each image. In order to maintain smoothness of the motility events bar, a term that controls the changes between the angles of strips selected from consecutive frames may be determined. Other cuts may be selected from images, and in some embodiments a combination of different types of cuts may be used to generate a motility events bar.

In operation 1440, the selected strips or lines (typically copies of the selected strips) may be aligned or positioned, for example vertically, and may be adjoined or positioned adjacently to each other, in order to form a visual representation of motility events which occurred in an image stream, e.g. motility events bar or display 2080. The strips or lines, or copies of the strips or lines, may be used to form a motility events bar. The length (and/or width) of the selected strips may be resized to different lengths, e.g. may be stretched or reduced.

Figure 10A:
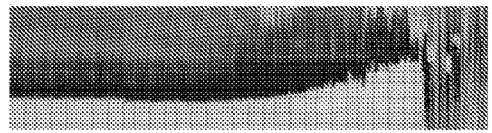
FIGS. 10A-10H show motility events bars generated from the same data using different cuts, according to embodiments of the present invention.
Figure 10B:
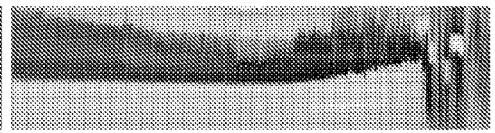
Figure 10C:
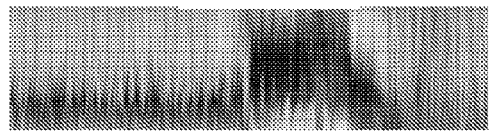
Figure 10D:
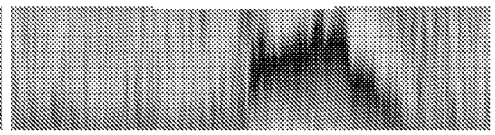
Figure 10E:
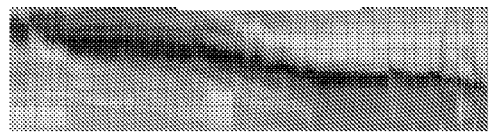
Figure 10F:
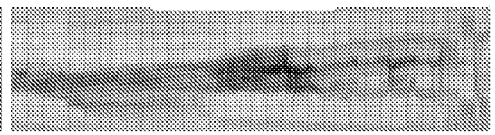
Figure 10G:
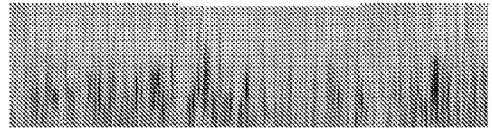
Figure 10H:
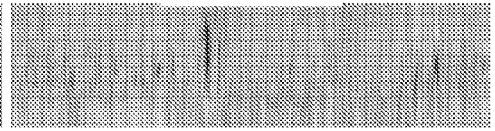

In operation 1450, the motility events bar may (optionally) be created or generated for display, for example on a visual display unit such as monitor 18. The motility events bar may be displayed, for example, alongside a window displaying a video view of the image stream, e.g. window 2001 shown in FIG. 1B. The motility events bar may be analyzed, and sequences of images may be correlated to certain motility events. For example, tunnel sequences may be detected for example as shown in FIGS. 10A and 10B. In another example, contraction rhythm analysis, e.g. analysis of different contractile frequency may be performed. In some embodiments, the motility events bar may be useful for visual validation of different motility properties or events such as contractions, turbid sequences, tunnel, static frames, etc.

The motility events bar may also be used for analysis of motility properties of the image stream. Motility events may be detected in the motility events bar, and may be indicated or labeled and displayed to a user. Different motility-related properties may be calculated and summarized, such as pattern, type, rhythm, frequency and/or duration of contractions, average duration of contraction, frequency of contractions in a certain region of the GI tract, etc. Other motility events may be detected and related properties may be calculated and presented or displayed. A range of normal and abnormal values may be presented to the user, for example along with the calculated property, to enable comparison between the normal range and the detected value of the property, and in some embodiments an indication may be provided regarding, for example, abnormal behavior which may have been detected.

Other operations or series of operations may be used.

Different embodiments are disclosed herein. Features of certain embodiments may be combined with features of other embodiments; thus certain embodiments may be combinations of features of multiple embodiments.

Embodiments of the invention may include an article such as a computer or processor readable non-transitory storage medium, such as for example a memory, a disk drive, or a USB flash memory encoding, including or storing instructions, e.g., computer-executable instructions, which when executed by a processor or controller, cause the processor or controller to carry out methods disclosed herein.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A computer-implemented method for display of intestinal motility events in an image stream captured by an in vivo imaging device, the method comprising:
   receiving an image stream captured by the in vivo device, the image stream comprising image frames, each image frame comprising a plurality of image pixels;
   detecting a predetermined feature in each image frame of at least a subset of the image stream;
   selecting a strip of pixels from each image frame of the at least subset of the image stream, such that the strip of pixels passes through the detected feature in each image frame;
   aligning the selected strips adjacently to form a motility events bar; and
   displaying the motility events bar on a visual display unit.

2. The method of claim 1 wherein the strip of pixels comprises at least one line of pixels selected from an image frame.

3. The method of claim 2 wherein the strip of pixels is a straight line of pixels.

4. The method of claim 1 comprising determining a fixed point in each image frame which is included in the selected strip of pixels.

5. The method of claim 4 wherein the fixed point is the center of the image frame.

6. The method of claim 1, wherein the predetermined feature is a lumen hole.

7. The method of claim 6, wherein the strip of pixels is selected to pass through the center of the detected lumen hole.

8. The method of claim 6, wherein the strip of pixels is selected such that the lumen length is maximized in the selected strip.

9. The method of claim 1, comprising displaying a video display of the image stream alongside the motility events bar.

10. The method of claim 1, comprising determining an intestinal event based on the motility events bar.

11. The method of claim 1, wherein the intestinal event is selected from: contraction, static closed lumen, tunnel and turbid lumen.

12. The method of claim 1, wherein the subset of image frames includes a sequence of consecutive image frames from the image stream.

13. A system for display of intestinal motility events in an image stream captured by an in vivo imaging device, comprising:
   a storage unit to store a plurality of image frames from the image stream, each image frame comprising a plurality of image pixels arranged in an array;
   a processor to:
      detect a predetermined feature in each image frame of at least a subset of the plurality of image frames;
      select a strip of pixels from each image frame of the at least subset of plurality of image frames, such that the strip of pixels passes through the detected feature in each image frame; and
      align the selected strips adjacently to form a motility events bar; and
   a visual display unit for displaying the motility events bar to a user.

14. The system of claim 13 wherein the strip of pixels comprises at least one line of pixels selected from an image frame.

15. The system of claim 14 wherein the strip of pixels is a straight line of pixels.

16. The system of claim 13 wherein the processor is to determine a fixed point in each image frame which is included in the selected strip of pixels.

17. The system of claim 16 wherein the fixed point is the center of the image frame.

18. The system of claim 13, wherein the predetermined feature is a lumen hole.

19. The system of claim 13, wherein the processor is to determine an intestinal event based on the motility events bar.

20. The system of claim 19, wherein the intestinal event is selected from: contraction, static closed lumen, tunnel and turbid lumen.

* * * * *